United States Patent
Nohira

(10) Patent No.: US 7,385,080 B2
(45) Date of Patent: Jun. 10, 2008

(54) METHOD FOR PRODUCING OPTICALLY ACTIVE β-PHENYLALANINE COMPOUNDS

(75) Inventor: Hiroyuki Nohira, Saitama (JP)

(73) Assignee: Ajinomoto Co., Inc., Tokyo (JP)

( * ) Notice: Subject to any disclaimer, the term of this patent is extended or adjusted under 35 U.S.C. 154(b) by 543 days.

(21) Appl. No.: 10/914,238

(22) Filed: Aug. 10, 2004

(65) Prior Publication Data

US 2005/0065366 A1    Mar. 24, 2005

Related U.S. Application Data

(63) Continuation of application No. PCT/JP03/01363, filed on Feb. 10, 2003.

(30) Foreign Application Priority Data

Feb. 15, 2002    (JP) .............................. 2002-038757

(51) Int. Cl.
C07B 57/00    (2006.01)
C07C 229/00    (2006.01)

(52) U.S. Cl. ...................... 562/401; 562/450
(58) Field of Classification Search ................ 562/401, 562/450
See application file for complete search history.

(56) References Cited

U.S. PATENT DOCUMENTS 3,996,288 A * 12/1976 Yukata et al. ................ 568/428
4,151,198 A    4/1979 Halmos

FOREIGN PATENT DOCUMENTS

| EP | 0 423 467 | 4/1991 |
|---|---|---|
| EP | 1 013 769 A1 | 6/2000 |
| HU | 37389 A | 4/1984 |
| HU | 37 389 | 12/1985 |
| JP | 62-114945 | 5/1987 |
| JP | 62-123156 | 6/1987 |
| JP | 11-043475 | 2/1999 |
| JP | 2002-533086 | 10/2002 |
| WO | WO 85/03932 | 9/1985 |
| WO | WO 00/37657 | 6/2000 |

OTHER PUBLICATIONS

Giuliana Cardillo et al, "A Stereoselective Synthesis of (2R,3S)-N-Benzoylphenylisoserine Methyl Ester", *J. Org. Chem.*, 1998, vol. 63, No. 7, pp. 2351-2353.
Kazuaki Ishihara et al, "A New Chiral BLA Promoter for Asymmetric Aza Diels-Alder and Aldol-Type Reactions of Imines", *J. Am Chem. Soc.*, 1994, vol. 116, No. 23, pp. 10520-10524.
W.M. Rodionow et al, "The Mechanism of Formation of Beta-Aryl-Beta-Amino Fatty Acids By The Condensation of Aromatic Aldehydes With Malonic Acid and Its Drivatives", *J. Am. Chem. Soc.*, Mar. 1929, vol. 51, pp. 841-847.
U.S. Appl. No. 10/914,238, filed Aug. 10, 2004, Nohira.
U.S. Appl. No. 10/915,436, filed Aug. 11, 2004, Nohira.
J. Gressay et al, Database Caplus Chemical Abstracts Service, XP-002315104, AN: 1986:515406, DN: 105:115406, Abstract for HU 37 389, 1985.
H. Nohira, Database Caplus Chemical Abstracts Service, XP-002315128, AN: 1999:114144, DN: 130:209981, Abstract for JP 11-043475, 1999.
A. Miyata et al, Database Caplus Chemical Abstracts Service, XP-002315105, AN: 1988:529683, DN: 109:129683, Abstract for JP 62-114945, 1987.

* cited by examiner

*Primary Examiner*—Taylor Victor Oh
(74) *Attorney, Agent, or Firm*—Oblon, Spivak, McClelland, Maier & Neustadt, P.C.

(57) ABSTRACT

Optically active β-phenylalanine compound may be prepared in an industrially advantageous manner by reacting an N-acyl-β-phenylalanine compound with a specific optically resolving agent to effect an optical resolution by formation of diastereomer salts, and removing the optically resolving agent from each diastereomer, to give an optically N-acyl-β-phenylalanine compound. Deacylation may be further carried out to obtain an optically active β-phenylalanine compound.

16 Claims, No Drawings

METHOD FOR PRODUCING OPTICALLY ACTIVE β-PHENYLALANINE COMPOUNDS

CROSS REFERENCES TO RELATED APPLICATIONS

This application is a continuation of International Patent Application No. PCT/JP03/01363, filed on Feb. 10, 2003, and claims priority to Japanese Patent Application No. 2002-038757, filed on Feb. 15, 2002, both of which are incorporated herein by reference in their entireties.

BACKGROUND OF THE INVENTION

1. Field of the Invention

The present invention relates to methods for producing optically active N-acyl-β-phenylalanine compounds. The present invention also relates to methods for producing optically active β-phenylalanine compounds. The present invention further relates to diastereomer salts of N-acyl-β-phenylalanine compounds, which are useful for preparing optically active N-acyl-β-phenylalanine compounds.

2. Discussion of the Background

Optically active β-phenylalanine compounds are known to be material for receptor antagonists and enzyme inhibitors and are compounds which are useful as intermediates for pharmaceuticals such as antithrombotic agents, etc. Known methods for the production of optically active β-phenylalanine compounds include a method in which a racemic β-phenylalanine compound is enzymatically resolved (see, for example, *J. Org. Chem.*, vol. 63, p. 2351 (1998), as a method using penicillin acylase), and a method in which the manufacture involves asymmetric synthesis (see, for example, *J. Am. Chem. Soc.*, vol. 116, p. 10520 (1994), as a method using an asymmetric aldol reaction), etc. However, it is difficult to obtain an optically active β-phenylalanine derivative having a high optical purity in an efficient manner. On the other hand, racemic β-phenylalanine derivatives may be relatively easily produced by synthetic means (see, for example, *J. Am. Chem. Soc.*, vol. 51, p. 841 (1929). Thus, there has been a demand for the development of a process for the optical resolution of a racemic substance for the production of optically active β-phenylalanine derivatives.

SUMMARY OF THE INVENTION

Accordingly, it is one object of the present invention to provide novel methods for making optically active β-phenylalanine derivatives.

It is another object of the present invention to provide novel industrially advantageous methods for making optically active β-phenylalanine derivatives.

It is another object of the present invention to provide novel methods for making optically active β-phenylalanine derivatives by deacylating an optically active N-acyl-β-phenylalanine derivative.

It is another object of the present invention to provide novel methods for making optically active N-acyl-β-phenylalanine derivatives.

It is another object of the present invention to provide novel methods for making optically active pharmaceutical compounds from optically active β-phenylalanine or a derivative thereof.

These and other objects, which will become apparent during the following detailed description, have been achieved by the inventor's discovery that an optically active N-acyl-β-phenylalanine derivative having a high optical purity may be obtained by converting an N-acyl-β-phenylalanine derivative, in which an amino group of the β-phenylalanine derivative is acylated, into diastereomers with a specific optically active compound (optically resolving agent), first selectively separating one of the diastereomers, then separating the other diastereomer, subjecting each of the separated salts to a double decomposition treatment, and then deacylating one or both of the obtained optically active N-acyl-β-phenylalanine derivatives.

Thus, the present invention provides the following:

(1) A method for producing an optically active N-acyl-β-phenylalanine compound represented by formula (4):

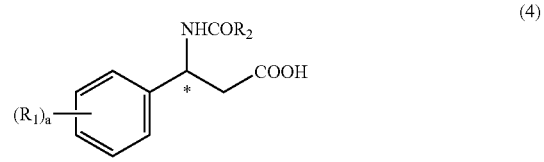

in which $R_1$ is hydrogen atom, halogen atom, nitro group, an alkyl group, or an alkoxy group; a is an integer of from 1 to 5; $R_2$ is hydrogen atom, an alkyl group, an aryl group, or an aralkyl group; and * means that that carbon atom is an asymmetric carbon atom, said method comprising:

(a) reacting an N-acyl-β-phenylalanine compound represented by formula (1):

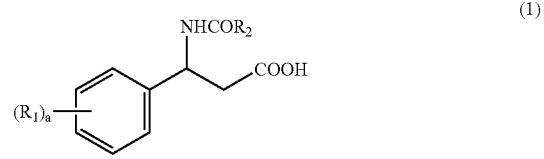

in which $R_1$, a, and $R_2$ are as defined above, with either an optically active compound represented by formula (2):

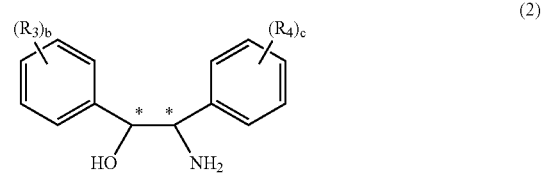

in which $R_3$ and $R_4$ each independently is hydrogen atom, halogen atom, nitro group, an alkyl group, or an alkoxy group; b and c are each independently integers of from 1 to 5; and * has the same meaning as defined above, or an optically active compound represented by formula (3):

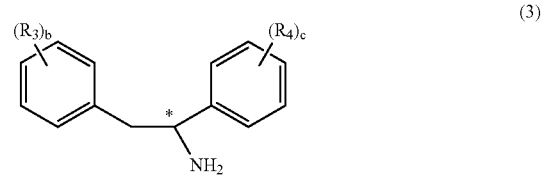

in which $R_3$, $R_4$, b, c, and * have the same meanings as defined above, to obtain a diastereomer salt;

(b) subjecting said diastereomer salt to an optical resolution, to obtain an optically active diastereomer salt; and (c) subjecting said optically active diastereomer salt to a double decomposition treatment.

(2) A method for producing an optically active N-acyl-β-phenylalanine compound represented by formula (4):

in which $R_1$ is hydrogen atom, halogen atom, nitro group, an alkyl group, or an alkoxy group; a is an integer of from 1 to 5; $R_2$ is hydrogen atom, an alkyl group, an aryl group, or an aralkyl group; and * means that that carbon atom is an asymmetric carbon atom, said method comprising:

(a) acylating the amino group of a β-phenylalanine compound represented by formula (5):

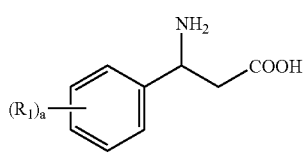

in which $R_1$ and a are as defined as above, to obtain an N-acyl-β-phenylalanine compound represented by formula (1):

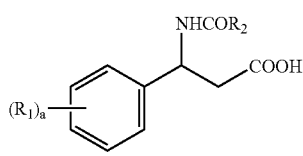

in which $R_1$, a, and $R_2$ are as defined above;

(b) reacting said N-acyl-β-phenylalanine compound of formula (1) with either an optically active compound represented by formula (2):

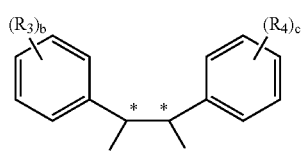

in which $R_3$ and $R_4$ each independently is hydrogen atom, halogen atom, nitro group, an alkyl group, or an alkoxy group; b and c are each independently an integer of from 1 to 5; and * means that that carbon atom is an asymmetric carbon atom, or an optically active compound represented by formula (3):

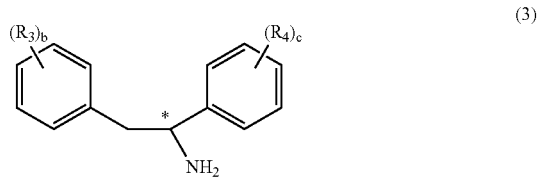

in which $R_3$, $R_4$, b, c, and * have the same meanings as defined above, to obtain a diastereomer salt;

(c) subjecting said diastereomer salt to an optical resolution, to obtain an optically active diastereomer salt; and (d) subjecting said optically active diastereomer salt to a double decomposition treatment.

(3) The method according to (1) or (2), wherein the optical resolution is carried out by crystallization of the diastereomer salt.

(4) A method for producing an optically active β-phenylalanine compound represented by formula (6):

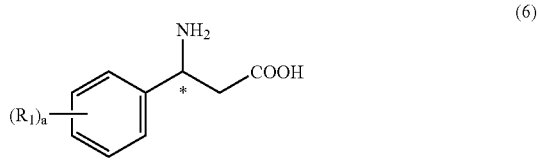

in which $R_1$ is hydrogen atom, halogen atom, nitro group, an alkyl group, or an alkoxy group; a is an integer of from 1 to 5; and * means that that carbon atom is an asymmetric carbon atom, said method comprising:

(a) preparing an optically active N-acyl-β-phenylalanine compound represented by formula (4):

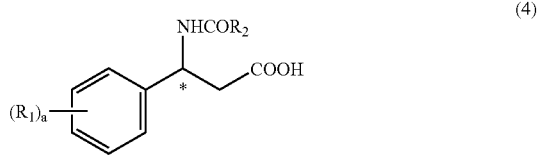

in which $R_2$ is hydrogen atom, an alkyl group, an aryl group, or an aralkyl group; and $R_1$, a, and * have the same meanings as above, according to any of the methods mentioned in the above (1) to (3); and (b) deacylating the optically active N-acyl-β-phenylalanine compound.

(5) A diastereomer salt, which is represented by formula (7):

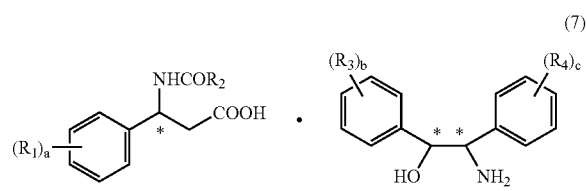

in which $R_1$ is hydrogen atom, halogen atom, nitro group, an alkyl group, or an alkoxy group; a is an integer of from 1 to 5; $R_2$ is hydrogen atom, an alkyl group, an aryl group, or an aralkyl group; $R_3$ and $R_4$ each independently is hydrogen atom, halogen atom, nitro group, an alkyl group, or an alkoxy group; b and c are each independently an integer of from 1 to 5; and * means that that carbon atom is an asymmetric carbon atom.

(6) A diastereomer salt which is represented by formula (8):

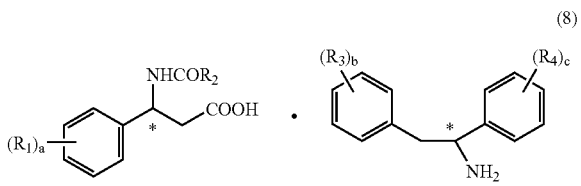

(8)

in which $R_1$ is hydrogen atom, halogen atom, nitro group, an alkyl group, or an alkoxy group; a is an integer of from 1 to 5; $R_2$ is hydrogen atom, an alkyl group, an aryl group, or an aralkyl group; $R_3$ and $R_4$ each independently is hydrogen atom, halogen atom, nitro group, an alkyl group, or an alkoxy group; b and c are each independently an integer of from 1 to 5; and * means that that carbon atom is an asymmetric carbon atom.

DETAILED DESCRIPTION OF THE PREFERRED EMBODIMENTS

Thus, in a first embodiment, the present invention provides novel methods for making an optically active β-phenylalanine derivative.

In the context of the present specification, a β-phenylalanine derivative means βphenylalanine having a substituent on its phenyl group (a β-phenylalanine derivative in a narrow sense) but, when there is no risk of misunderstanding in terms of the context, the β-phenylalanine derivative in a narrow sense and β-phenylalanine together may be referred to as a β-phenylalanine derivative (a broad sense).

The present invention will now be illustrated in more detail below.

The term optical resolution is defined as follows. "Optical resolution—An operation by which a racemic substance is separated into each enantiomer, i.e. optical isomer, is called an optical resolution. In an optical resolution, there is a direct method where a racemic substance is directly resolved into optical isomers and a method where a racemic substance is made to react with an optically active reagent (optical resolving agent) to give diastereomers, resolution into each diastereomer is conducted utilizing the difference in physical property between the diastereomers and the optically active reagent is removed to give an optically active substance. Representative means in the direct method are a preferential crystallization where crystals of an optical active substance (crystal seeds) are added to a saturated solution of a racemic substance to promote the crystallization whereupon an optical active substance is prepared (preferential crystallization method) and a column chromatography where an optically active stationary phase is used. When a racemic substance is an acid for example, a typical method for the preparation of a diastereomer is that a diastereomer salt with an optically active base such as alkaloid (e.g., quinine and brucine) is prepared, recrystallization is conducted to separate it as a pure desired diastereomer salt and the resulting salt is decomposed with an acid or an alkali to give an optically active substance." ("Kagaku Jiten" (*Encyclopedic Dictionary of Chemistry*), page 458, published by Tokyo Kagaku Dojin in 1994).

Among the optically resolving methods as illustrated above, the method for producing an optically-active N-acyl-β-phenylalanine compound according to the present invention utilizes an optically resolving agent (which may also be abbreviated as a diastereomer method). It should be noted that an important point in the development of the diastereomer method is that other operation conditions per se may be in accordance with the conventional methods in an appropriate manner.

Now, in the β-phenylalanine compound represented by the above formula (5) in the present invention (and the corresponding optically active substances thereof represented by the above formula (6)), $R_1$ is hydrogen atom, halogen atom, nitro group, an alkyl group, or an alkoxy group. Examples of the halogen group are chlorine atom, bromine atom, fluorine atom, iodine atom, etc. Examples of the alkyl group are $C_{1-6}$ alkyl groups such as methyl group, ethyl group, propyl group, and butyl group. Examples of the alkoxy group are $C_{1-6}$ alkoxy groups such as methoxy group and ethoxy group. The alkyl group and the alkoxy group as such may have one or more substituents such as a halogen atom. The β-phenylalanine derivative which is most preferably used as a starting material in the present production method according to the present invention is β-phenylalanine (or 3-amino-3-phenylpropanoic acid) where $R_1$ is hydrogen atom.

$R_1$ in the N-acyl-β-phenylalanine compounds represented by the above formula (1) (and the corresponding optically active substance thereof represented by the above formula (4)) in the present invention is the same as that mentioned already. $R_2$ is hydrogen atom, an alkyl group, an aryl group, or an aralkyl group. Examples of the alkyl group in $R_2$ are $C_{1-6}$ alkyl groups such as methyl group, ethyl group, and propyl group; examples of the aryl group therein are $C_{6-10}$ aryl groups such as phenyl group and naphthyl group; and examples of the aralkyl group therein are $C_{7-11}$ aralkyl groups such as benzyl group. Those groups may have one or more substituents such as halogen atom. The N-acyl-β-phenylalanine compounds which are preferably used as the starting material in the production method of the present invention are N-acetyl-β-phenylalanine (or 3-acetylamino-3-phenylpropanoic acid) where $R_1$ is hydrogen atom and $R_2$ is methyl group and N-formyl-β-phenylalanine (or 3-formylamino-3-phenylpropanoic acid) where $R_1$ and $R_2$ are both hydrogen atoms. It is particularly preferable to use N-acetyl-β-phenylalanine.

In the optically active compound (optically resolving agent) represented by the above formula (2) or (3) in the present invention, $R_3$ and $R_4$ each independently is hydrogen atom, halogen atom, nitro group, an alkyl group, or an alkoxy group. Examples of the halogen group are chlorine atom, bromine atom, fluorine atom, iodine atom, etc. Examples of the alkyl group are $C_{1-6}$ alkyl groups such as methyl group, ethyl group, propyl group, and butyl group. Examples of the alkoxy group are $C_{1-6}$ alkoxy groups such as methoxy group and ethoxy group. These alkyl groups and alkoxy groups may have one or more substituents such as a halogen atom.

The optically active compounds (optically resolving agent) represented by the above formula (2) or (3) which are particularly preferred for use in the formation of the diastereomer salt in the present invention are 2-amino-1,2- diphenylethanol and 2-(4-methylphenyl)-1-phenylethylamine where both $R_3$ and $R_4$ are hydrogen atoms. For N-formyl-β-phenylalanine and N-acetyl-β-phenylalanine, 2-(4-methylphenyl)-1-phenylethylamine and 2-amino-1,2-diphenylethanol are particularly preferably used, respectively.

The configuration of the optically active compound represented by the above formula (2) or (3) (optically resolving agent) may be appropriately selected depending upon the desired configuration of the optically active N-acyl-β-phenylalanine compound or optically active β-phenylalanine compound. Thus, for example, (+)-3-acetylamino-3-phenylpropanoic acid may be prepared using (1R,2S)-(−)-2-amino-1,2-diphenylethanol while (−)-3-acetylamino-3-phenylpropanoic acid may be prepared using (1S,2R)-(+)-2-amino-1,2-diphenylethanol. Further, for example, (+)-3-formylamino-3-phenylpropanoic acid may be prepared using (S)-(+)-2-(4-methylphenyl)-1-phenylethylamine while (−)-3-formylamino-3-phenylpropanoic acid may be prepared using (R)-(−)-2-(4-methylphenyl)-1-phenylethylamine.

In the compounds according to the present invention, a, b, and c are each independently of each other an integer of 1 to 5, i.e., each phenyl group may contain one or more substituents. In other words, each phenyl ring many be substituted with one of $R_1$, $R_3$, and $R_4$, or a plurality of such substituents. In that case, the substituents on a given phenyl group may be the same or different. Moreover, the phenyl rings may be substituted in any of the ortho-, meta-, and/or para-positions.

The N-acyl-β-phenylalanine compound which is represented by the above formula (1) and used as a starting material in the production method of the present invention and the optically active compound (optically resolving agent) which is represented by the above formula (2) or (3) and used for the formation of the diastereomer salt may be used in a form of a salt so long as the advantage of the present invention is still achieved. The optically active N-acyl-β-phenylalanine compound represented by the above formula (4) and the optically active β-phenylalanine compound represented by the above formula (6) which are the desired substances may be separated and prepared in such a manner that the diastereomer salt is subjected to a double decomposition treatment and then the desired substance is converted into the form of appropriate another salt from the decomposed solution if necessary. Thus, such embodiments are also within a scope of the present invention.

There is no particular limitation of the method for acylating the β-phenylalanine compound represented by the above formula (5); any method which is known by persons skilled in the art may be appropriately used. For example, the product may be prepared by the reaction of a β-phenylalanine compound using a carboxylic acid represented by formula (9):

$$R_2\text{—COOH} \quad (9)$$

as an acylating agent. In formula (9), $R_2$ has the same meaning as defined already.

The formation of a diastereomer salt by the reaction the N-acyl-β-phenylalanine compound represented by the above formula (1) with the optically active compound (optically resolving agent) represented by the above formula (2) or (3) may be carried out after dissolving them in an appropriate solvent. It is not always necessary that the N-acyl-β-phenylalanine derivative is a racemic compound but a substance in which the amount of one of the optically active substances is more than that of another optically active substance (antipode) may also be subjected to the method of the present invention for preparing one optically active compound.

The amount of the optically active compound (optically resolving agent) represented by the above formula (2) or (3) is usually within a range of 0.2 to 3 mol or, preferably, 0.5 to 1.5 mol to 1 mol of the N-acyl-β-phenylalanine compound represented by the above formula (1).

There is no particular limitation for the solvent used therefor so far as it is able to dissolve the N-acyl-β-phenylalanine compound represented by the above formula (1) and the optically active compound (optically resolving agent) represented by the above formula (2) or (3). Examples of preferred solvents are methanol, ethanol, isopropanol, acetone, methyl ethyl ketone and ethyl acetate, and the particularly preferred one is methanol. Although there is no particular limitation for the amount of the solvent used, it is usually used within a range of 1- to 50-fold by weight based on the weight of the N-acyl-β-phenylalanine represented by the above formula (1).

After that, the thus-formed two kinds of diastereomer salts are subjected to an optical resolution so that one of the diastereomer salts is selectively separated. The optical resolution may be carried out by means of crystallization in an appropriate solvent. Examples of the preferred solvent for the crystallization are methanol, ethanol, isopropanol, acetone, methyl ethyl ketone, and ethyl acetate and the particularly preferred one is ethanol. Although there is no particular limitation for the amount of the solvent used, it is usually used within a range of 1- to 50-fold by weight based on the weight of the N-acyl-β-phenylalanine represent by the above formula (1). It is also possible that the same solvent that is used for the formation of the salt may be used for the crystallization, whereby salt formation and crystallization may be carried out continuously. It is further possible that, after formation of the salt, the solvent is evaporated, and crystallization is conducted using another solvent. Incidentally, crystals of the resulting diastereomer may also be further purified by dissolving them in an appropriate solvent and subject them to a crystallization once again.

The resulting diastereomer salt crystals are subjected to a double decomposition treatment by known methods such as a double decomposition treatment with an acid or a base or a decomposition treatment with ion-exchange resin (this is also a kind of double decomposition treatment), whereupon the optically active N-acyl-β-phenylalanine compound represented by the above formula (4) is prepared.

In the case of a double decomposition with a base for example, the diastereomer salt is dissolved in an aqueous solution, a basic aqueous layer is extracted with an organic solvent (whereby the optical resolving agent is transferred to the organic solvent layer), and an acid is added to the aqueous layer to make the aqueous layer acidic. The resulting acidic aqueous layer is extracted with an organic solvent, and then the organic solvent is evaporated in vacuo from the extract to give the desired optically active N-acyl-β-phenylalanine compound. Examples of the base used here are sodium hydroxide, potassium hydroxide, magnesium hydroxide, calcium hydroxide, sodium carbonate, potassium carbonate, sodium hydrogen carbonate, and potassium hydrogen carbonate, and the particularly preferably used ones are sodium hydroxide and potassium hydroxide. With regard to the acid, hydrochloric acid, sulfuric acid, etc. are preferably used. Examples of the organic solvent used for the extraction are diethyl ether, tetrahydrofuran, ethyl acetate, n-hexane, n-heptane, cyclohexane, toluene, xylene, dichloromethane, and dichloroethane. The amount of the base or the acid used is usually within a range of 1 to 200 mol to one mol of the diastereomer salt being subjected to the double decomposition, while amount of the organic solvent used is usually within a range of 1- to 100-fold in terms of weight ratio to the diastereomer salt being subjected to the same treatment.

The optically active N-acyl-β-phenylalanine compound which is prepared as such may be further purified, if necessary, by recrystallization from an appropriate solvent such as ethanol.

It is also possible that the optically active compound represented by the above formula (2) or (3) is recovered for recycling from the mother liquor, etc. after the double decomposition treatment.

The other diastereomer, which is an antipode, is contained in the mother liquor (filtrate) obtained in the step, in which the diastereomers are formed and one of the diastereomer salts is separated as crystals, and, therefore, it is also possible that the solvent may be evaporated therefrom in vacuo, and the resulting residue subjected to the same double decomposition treatment as above, to obtain the other enantiomer of the above-prepared optically N-acyl-β-phenylalanine compound. In order to enhance its optical purity if necessary, it is preferred that the resulting enantiomer is purified by recrystallization using an appropriate solvent such as ethanol.

When the resulting optically active N-acyl-β-phenylalanine compound represented by the above formula (4) is subjected to a deacylation reaction known by persons skilled in the art, such as a deacylation using an acid, an optically active β-phenylalanine compound represented by the above formula (6) is prepared.

It is preferred that the optically active β-phenylalanine or derivative thereof prepared according to the present invention have an enantiomeric excess of at least 50%, preferably at least 70%, more preferably at least 80%, even more preferably at least 90%, even more preferably at least 95%.

The optically active β-phenylalanine or derivative thereof produced according to the present invention may be used for making a compound of the formula (9), (10), or (11), and pharmaceutically acceptable salts thereof:

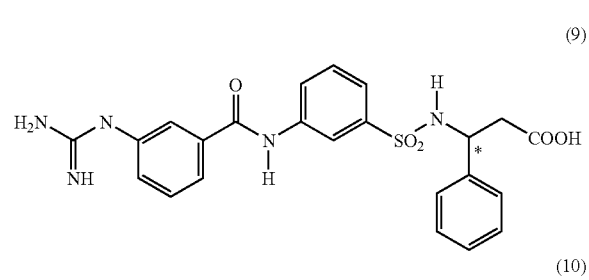

(9)

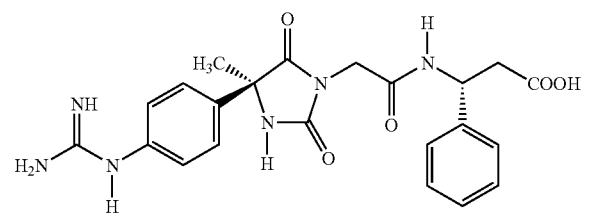

(10)

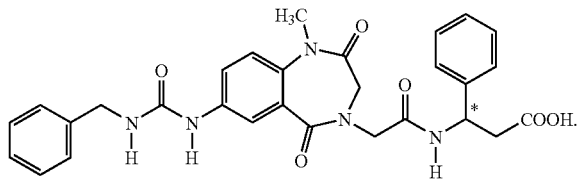

(11)

Other features of the invention will become apparent in the course of the following descriptions of exemplary embodiments which are given for illustration of the invention and are not intended to be limiting thereof.

EXAMPLES

In the following examples, the optical purity of the resulting substances was determined by means of a high-performance liquid chromatography using an optically active column.

Example 1

N-Acetylation of β-phenylalanine (±)-3-Amino-3-phenylpropanoic acid (2.378 g, 14.4 mmol), 2.0 ml of acetic acid, and 236 mg (2.88 mmol) of anhydrous sodium acetate were charged into a 30-ml two-necked round-bottomed flask equipped with a stirrer and a calcium chloride tube and cooled down to a temperature not higher than 10° C. using an ice bath. Acetic anhydride (4 ml, 42.8 mmol) cooled to a temperature of not higher than 10° C. was added dropwise to the solution, and the mixture was stirred for 40 minutes at that temperature and then stirred for 80 minutes at room temperature.

After completion of the reaction, the reaction solution was washed with distilled water and extracted with ethyl acetate. After that, the extract was dried for one night over anhydrous sodium sulfate, and the solvent was evaporated in vacuo. The residue was recrystallized from 99% ethanol to give 2.40 g (11.6 mmol) of (±)-3-acetylamino-3-phenylpropanoic acid in a yield of 80.5% (melting point: 161 to 162° C.).

Example 2

Optical Resolution of N-acetyl-β-phenylalanine by a Diastereomer Method

Each of 622 mg (3.0 mmol) of (±)-3-acetylamino-3-phenylpropanoic acid and 640 mg (3.03 mmol) of (1R,2S)-(−)-erythro-2-amino-1,2-diphenylethanol (the chemical formula thereof is given at the end of this Example) were dissolved in an appropriate amount of ethanol to form diastereomer salts. The solvent was evaporated in vacuo from the resulting solution, and the residue was placed in a 30-ml Erlenmeyer flask equipped with an Allihn condenser and heated to reflux after addition of 7.0 ml of 99% ethanol to completely dissolve.

The solution was allowed to stand for one night, and the separated crystals were dried under reduced pressure in a desiccator for one night to give 621 mg (1.48 mmol) of crude crystals of (+)-3-acetylamino-3-phenylpropanoic acid and (1R,2S)-(−)-erythro-2-amino-1,2-diphenylethanol. The resulting crude crystals were recrystallized from 99% ethanol, and the crystals were filtered to give 435 mg (1.03 mmol) of the salt crystals in a yield of 68.7% (melting point: 163 to 164° C., $[\alpha]_D=-30.3°$ (c=1.0, methanol)).

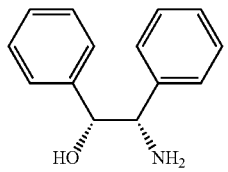

(1R,2S)-(−)-erythro-2-amino-1,2-diphenylethanol

Example 3

Preparation of an Optically Active N-acetyl-β-phenylalanine by a Double Decomposition of the Salt The salt prepared in Example 2 was subjected to a double decomposition with a 1M aqueous solution of sodium hydroxide, and a basic organic substance was extracted from the double-decomposed solution with ether. To the aqueous layer after extracting with ether, 1M of hydrochloric acid was added to achieve the Congo Red acidic property, the organic substance was extracted with ethyl acetate, and the extract was dried by addition of anhydrous sodium sulfate thereto. After that, ethyl acetate was evaporated in vacuo to give 174 mg (0.840 mmol) of (+)-3-acetylamino-3-phenylpropanoic acid in a yield of 56.0% (melting point: 190 to 191° C., $[\alpha]_D=-84.9°$ (c=0.6, methanol), optical purity >99.0% e.e.).

Example 4

Preparation of an Optically Active N-acetyl-β-phenylalanine which is an Antipode The filtrate obtained in Example 2 was combined and concentrated in vacuo to give 834 mg of a residue containing (−)-3-acetylamino-3-phenylpropanoic acid and (1R,2S)-(−)-erythro-2-amino-1,2-diphenylethanol diastereomer salts. That was subjected to the same double decomposition treatment as in Example 3 to give 326 mg of crude (−)-3-acetylamino-3-phenylpropanoic acid (optical purity: 59.5%). This was recrystallized from 99% ethanol to give 151 mg (0.729 mmol) of (−)-3-acetylamino-3-phenylpropanoic acid in a yield of 48.6% (melting point: 191 to 192° C., $[\alpha]_D=-84.5°$(c=0.1, methanol), optical purity >99.0% e.e.).

Example 5

Deacetylation of N-acetyl-β-phenylalanine (+)-3-acetylamino-3-phenylpropanoic acid (207 mg, 1.00 mmol) prepared by the same manner as in Example 3 and 2.0 ml of 2M hydrochloric acid were added to a 30-ml two-necked flask equipped with a stirrer and heated to reflux for 3 hours. After 3 hours, 1 drop of concentrated hydrochloric acid was added to the reaction solution using a Pasteur pipette and the mixture was heated to reflux for 2 hours more. After completion of the reaction, the reaction solution was evaporated to dryness in vacuo, and the resulting residue was washed with a mixed solvent of methanol/diisopropyl and recrystallized from a mixed solvent of 2-propanol/99% ethanol to give 79 mg (0.392 mmol) of (+)-3-amino-3-phenylpropanoic acid hydrochloride in a yield of 39.2% (melting point: 195 to 196° C., $[\alpha]_D=-3.03°$ (c=1.0, methanol)).

Example 6

N-Formylation of β-phenylalanine

Formic acid (1.0 ml, 26.6 mmol) was added dropwise to 2.0 ml (21.4 mmol) of acetic anhydride in an ice bath. After that, the ice bath was removed, and the solution was stirred at 50° C. for 15 minutes. After allowing to stand for 15 minutes, the resulting solution was cooled again with an ice bath and was added dropwise to a solution of 586 mg (3.55 mmol) of (±)-3-amino-3-phenylpropanoic acid in 0.5 ml of formic acid previously cooled to a temperature not higher than 10° C. The mixture was stirred for 40 minutes as it was, and, when the solution became room temperature, it was stirred for 80 minutes more. The residue prepared by concentrating the reaction solution in vacuo was recrystallized from water to give 624 mg (3.23 mmol) of (±)-3-formylamino-3-phenylpropanoic acid in a yield of 91.0% (melting point: 127 to 128° C.).

Example 7

Optical Resolution of N-formyl-β-phenylalanine by a Diastereomer Method

Each of 579 mg (3.0 mmol) of (±)-3-formylamino-3-phenylpropanoic acid and 634 mg (3.0 mmol) of (R)-(−)-2-(4-methylphenyl)-1-phenylethylamine (the chemical formula thereof is given at the end of this Example) were dissolved in an appropriate amount of methanol to form diastereomer salts. The solvent was evaporated in vacuo from the resulting solution, and the residue was placed in a 10-ml Erlenmeyer flask equipped with an Allihn condenser and heated to reflux after addition of 1.8 ml of 99% ethanol to completely dissolve.

The solution was allowed to stand for one night, and the separated crystals were dried under reduced pressure in a desiccator for one night to give 617 mg (1.53 mmol) of crude crystals of (−)-3-formylamino-3-phenylpropanoic acid and (R)-(−)-2-(4-methylphenyl)-1-phenylethylamine. The resulting crude crystals were recrystallized from 99% ethanol three times, and the crystals were filtered to give 230 mg (0.57 mmol) of the salt crystals in a yield of 37.9% (melting point: 160 to 161° C., $[\alpha]_D=-105°$ (c=1.0, methanol)).

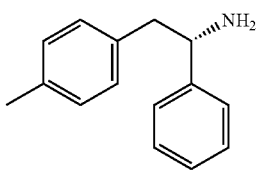

(R)-(−)-2-(4-methylphenyl)-1-phenylethylamine

Example 8

Preparation of an Optically Active N-formyl-β-phenylalanine by a Double Decomposition of the Salt The salt obtained in Example 7 was subjected to a double decomposition using a 1M aqueous solution of sodium hydroxide, and a basic organic substance was extracted from the double decomposed solution with ether. The aqueous layer after extracting with ether was made acidic to Congo Red, the organic substance was extracted with ethyl acetate, and the extract was dried by addition of anhydrous sodium sulfate thereto. After that, ethyl acetate was evaporated in vacuo from the dried extract to give 92 mg (0.476 mmol) of (−)-3-formylamino-3-phenylpropanoic acid in a yield of 31.7% (melting point: 135 to 136° C., $[\alpha]_D = -111°$ (c=0.5, methanol), optical purity >99.0% e.e.).

INDUSTRIAL APPLICABILITY

In accordance with the method of the present invention, an optically active N-acyl-β-phenylalanine compound and also an optically active β-phenylalanine compound may be prepared in an efficient manner and an industrially excellent method for the production thereof is provided.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

What is claimed is:

1. A method for making an optically active N-acyl-β-phenylalanine compound represented by formula (4):

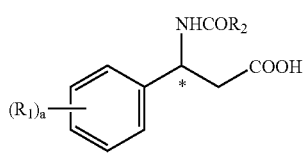

wherein $R_1$ is hydrogen atom, halogen atom, nitro group, a $C_{1-6}$ alkyl group, or a $C_{1-6}$ alkoxy group; a is an integer of from 1 to 5; $R_2$ is hydrogen atom, a $C_{1-6}$ alkyl group, a $C_{6-10}$ aryl group, or a $C_{7-11}$ aralkyl group; and * means that that carbon atom is an asymmetric carbon atom, said method comprising:
(a) reacting an N-acyl-β-phenylalanine compound represented by formula (1):

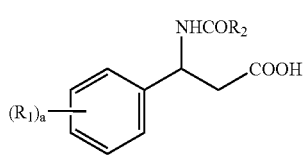

wherein $R_1$, a, and $R_2$ are as defined above, with either an optically active compound represented by formula (2):

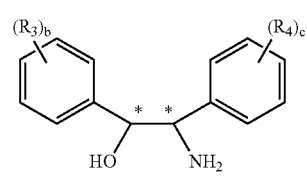

wherein $R_3$ and $R_4$ each independently is hydrogen atom, halogen atom, nitro group, a $C_{1-6}$ alkyl group, or a $C_{1-6}$ alkoxy group; b and c are each independently an integer of from 1 to 5; and * has the same meaning as defined above, or an optically active compound represented by formula (3):

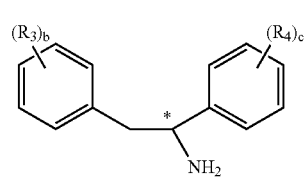

wherein $R_3$, $R_4$, b and c, and * have the same meanings as defined above, to obtain a diastereomer salt;

(b) subjecting said diastereomer salt to an optical resolution, to obtain an optically active diastereomer salt; and (c) subjecting said optically active diastereomer salt to a double decomposition treatment, to obtain said optically active N-acyl-β-phenylalanine compound represented by formula (4).

2. The method of claim 1, wherein said optical resolution comprises crystallizing said optically active diastereomer salt.

3. A method for making an optically active N-acyl-β-phenylalanine compound represented by formula (4):

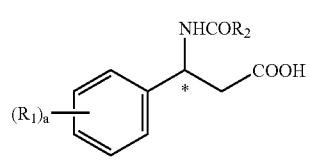

wherein $R_1$ is hydrogen atom, halogen atom, nitro group, a $C_{1-6}$ alkyl group, or a $C_{1-6}$ alkoxy group; a is art integer of from 1 to 5; $R_2$ is hydrogen atom, a $C_{1-6}$ alkyl group, a $C_{6-10}$ aryl group, or a $C_{7-11}$ aralkyl group; and * means that that carbon atom is an asymmetric carbon atom, said method comprising:
(a) acylating the amino group of a β-phenylalanine compound represented by formula (5):

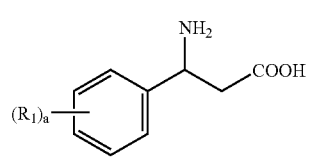

wherein $R_1$ and a are defined as above, to obtain an N-acyl-β-phenylalanine compound represented by formula (1):

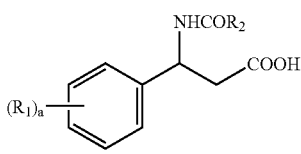

wherein $R_1$, a, and $R_2$ are as defined above;
(b) reacting said N-acyl-β-phenylalanine compound of formula (1) with either an optically active compound represented by formula (2):

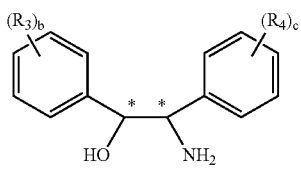

wherein $R_3$ and $R_4$ each independently is hydrogen atom, halogen atom, nitro group, a $C_{1-6}$ alkyl group, or a $C_{1-6}$ alkoxy group; b and c are each independently an integer of from 1 to 5;
and * means that that carbon atom is an asymmetric carbon atom,
or an optically active compound represented by formula (3):

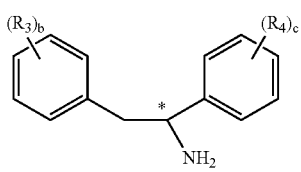

wherein $R_3$, $R_4$, b and c, and * have the same meanings as defined above, to obtain a diastereomer salt;
(c) subjecting said diastereomer salt to an optical resolution, to obtain an optically active diastereomer salt; and
(d) subjecting said optically active diastereomer salt to a double decomposition treatment, to obtain said optically active N-acyl-β-phenylalanine compound represented by formula (4).

4. The method of claim 3, wherein said optical resolution comprises crystallizing said optically active diastereomer salt.

5. A diastereomer salt, which is represented by formula (7):

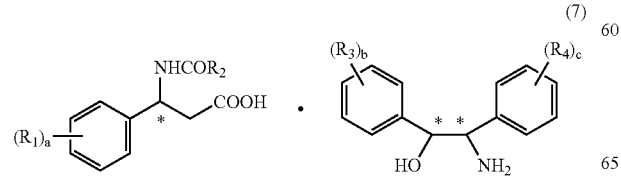

wherein $R_1$ is hydrogen atom, halogen atom, nitro group, a $C_{1-6}$ alkyl group, or a $C_{1-6}$ alkoxy group; a is an integer of from 1 to 5; $R_2$ is hydrogen atom, a $C_{1-6}$ alkyl group, a $C_{6-10}$ aryl group, or a $C_{7-11}$ aralkyl group; $R_3$ and $R_4$ each independently is hydrogen atom, halogen atom, nitro group, a $C_{1-6}$ alkyl group, or a $C_{1-6}$ alkoxy group; b and c are each independently an integer of from 1 to 5; and * means that that carbon atom is an asymmetric carbon atom.

6. The diastereomer salt of claim 5, wherein $R_1$ is hydrogen and $R_2$ is hydrogen or methyl.

7. A method of making a diastereomer salt, which is represented by formula (7):

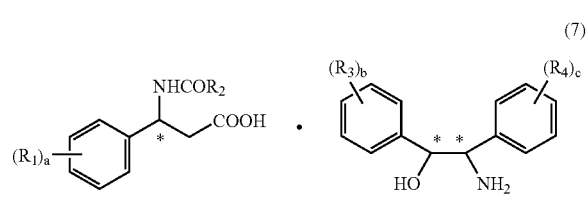

wherein $R_1$ is hydrogen atom, halogen atom, nitro group, a $C_{1-6}$ alkyl group, or a $C_{1-6}$ alkoxy group; a is an integer of from 1 to 5; $R_2$ is hydrogen atom, a $C_{1-6}$ alkyl group, a $C_{6-10}$ aryl group, or a $C_{7-11}$ aralkyl group; $R_3$ and $R_4$ each independently is hydrogen atom, halogen atom, nitro group, a $C_{1-6}$ alkyl group, or a $C_{1-6}$ alkoxy group; b and c are each independently an integer of from 1 to 5; and * means that that carbon atom is an asymmetric carbon atom, said method comprising:
(a) reacting an N-acyl-β-phenylalanine compound of formula (1):

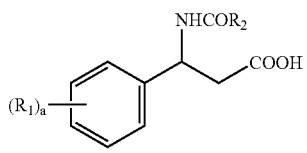

wherein $R_1$, a, and $R_2$ are as defined above;
with an optically active compound represented by formula (2):

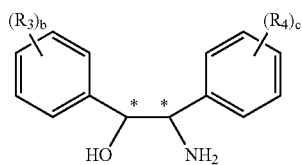

wherein $R_3$, $R_4$, b, c, and * are as defined above, to obtain a diastereomer salt; and
(b) subjecting said diastereomer salt to an optical resolution, to obtain said diastereomer salt of formula (7).

8. A diastereomer salt which is represented by formula (8):

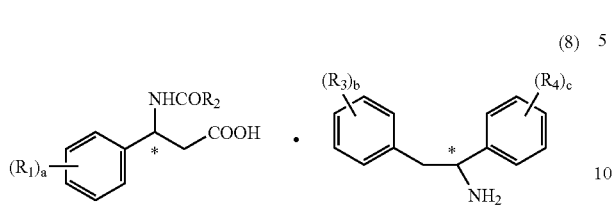

wherein $R_1$ is hydrogen atom, halogen atom, nitro group, a $C_{1-6}$ alkyl group, or a $C_{1-6}$ alkoxy group; a is an integer of from 1 to 5; $R_2$ is hydrogen atom, a $C_{1-6}$ alkyl group, a $C_{6-10}$ aryl group, or a $C_{7-11}$ aralkyl group; $R_3$ and $R_4$ each independently is hydrogen atom, halogen atom, nitro group, a $C_{1-6}$ alkyl group, or a $C_{1-6}$ alkoxy group; b and c are each independently an integer of from 1 to 5; and * means that that carbon atom is an asymmetric carbon atom.

9. The diastereomer salt of claim 8, wherein $R_1$ is hydrogen and $R_2$ is hydrogen or methyl.

10. A method of making a diastereomer salt which is represented by formula (8):

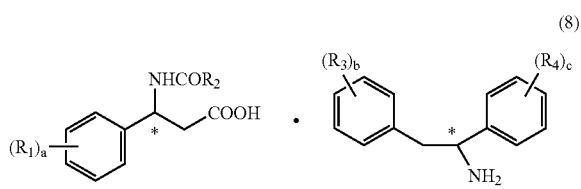

wherein $R_1$ is hydrogen atom, halogen atom, nitro group, a $C_{1-6}$ alkyl group, or a $C_{1-6}$ alkoxy group; a is an integer of from 1 to 5; $R_2$ is hydrogen atom, a $C_{1-6}$ alkyl group, a $C_{6-10}$ aryl group, or a $C_{7-11}$ aralkyl group; $R_3$ and $R_4$ each independently is hydrogen atom, halogen atom, nitro group, a $C_{1-6}$ alkyl group, or a $C_{1-6}$ alkoxy group; b and c are each independently an integer of from 1 to 5; and * means that that carbon atom is an asymmetric carbon atom, said method comprising:

(a) reacting an N-acyl-β-phenylalanine compound of formula (1):

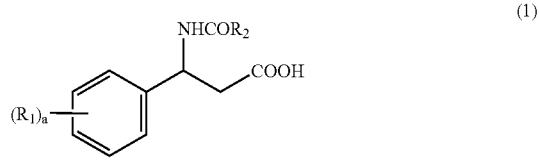

wherein $R_1$, a, and $R_2$ are as defined above;

with an optically active compound represented by formula (3):

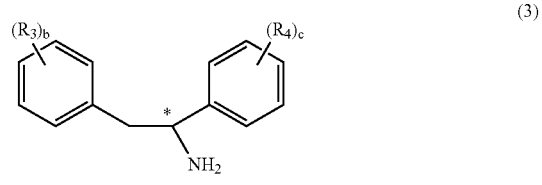

wherein $R_3$, $R_4$, b, c, and * are as defined above, to obtain a diastereomer salt; and (b) subjecting said diastereomer salt to an optical resolution, to obtain said diastereomer salt of formula (8).

11. The method of claim 1, wherein $R_1$ is hydrogen atom, halogen atom, nitro group, methyl group, ethyl group, propyl group, butyl group, methoxy group, or ethoxy group; $R_2$ is hydrogen atom, methyl group, ethyl group, propyl group, phenyl group, naphthyl group, or benzyl group; and $R_3$ and $R_4$ each independently is hydrogen atom, halogen atom, nitro group, methyl group, ethyl group, propyl group, butyl group, methoxy group, or ethoxy group.

12. The method of claim 3, wherein $R_1$ is hydrogen atom, halogen atom, nitro group, methyl group, ethyl group, propyl group, butyl group, methoxy group, or ethoxy group; $R_2$ is hydrogen atom, methyl group, ethyl group, propyl group, phenyl group, naphthyl group, or benzyl group; and $R_3$ and $R_4$ each independently is hydrogen atom, halogen atom, nitro group, methyl group, ethyl group, propyl group, butyl group, methoxy group, or ethoxy group.

13. The diastereomer salt of claim 5, wherein $R_1$ is hydrogen atom, halogen atom, nitro group, methyl group, ethyl group, propyl group, butyl group, methoxy group, or ethoxy group; $R_2$ is hydrogen atom, methyl group, ethyl group, propyl group, phenyl group, naphthyl group, or benzyl group; and $R_3$ and $R_4$ each independently is hydrogen atom, halogen atom, nitro group, methyl group, ethyl group, propyl group, butyl group, methoxy group, or ethoxy group.

14. The method of claim 7, wherein $R_1$ is hydrogen atom, halogen atom, nitro group, methyl group, ethyl group, propyl group, butyl group, methoxy group, or ethoxy group; $R_2$ is hydrogen atom, methyl group, ethyl group, propyl group, phenyl group, naphthyl group, or benzyl group; and $R_3$ and $R_4$ each independently is hydrogen atom, halogen atom, nitro group, methyl group, ethyl group, propyl group, butyl group, methoxy group, or ethoxy group.

15. The diastereomer salt of claim 8, wherein $R_1$ is hydrogen atom, halogen atom, nitro group, methyl group, ethyl group, propyl group, butyl group, methoxy group, or ethoxy group; $R_2$ is hydrogen atom, methyl group, ethyl group, propyl group, phenyl group, naphthyl group, or benzyl group; and $R_3$ and $R_4$ each independently is hydrogen atom, halogen atom, nitro group, methyl group, ethyl group, propyl group, butyl group, methoxy group, or ethoxy group.

16. The method of claim 10, wherein $R_1$ is hydrogen atom, halogen atom, nitro group, methyl group, ethyl group, propyl group, butyl group, methoxy group, or ethoxy group; $R_2$ is hydrogen atom, methyl group, ethyl group, propyl group, phenyl group, naphthyl group, or benzyl group; and $R_3$ and $R_4$ each independently is hydrogen atom, halogen atom, nitro group, methyl group, ethyl group, propyl group, butyl group, methoxy group, or ethoxy group.

* * * * *